US012594262B2

(12) United States Patent
Franklin et al.

(10) Patent No.: US 12,594,262 B2
(45) Date of Patent: Apr. 7, 2026

(54) CAI NANOEMULSIONS

(71) Applicant: ForwardVue Pharma, Inc., Mobile, AL (US)

(72) Inventors: Alan J. Franklin, Mobile, AL (US); Laurent Balenci, Mobile, AL (US); Srikanth Kakamanu, Mobile, AL (US); Robert Dempsey, Mobile, AL (US)

(73) Assignee: ForwardVue Pharma, Inc., Mobile, AL (US)

( * ) Notice: Subject to any disclaimer, the term of this patent is extended or adjusted under 35 U.S.C. 154(b) by 878 days.

(21) Appl. No.: 17/785,842

(22) PCT Filed: Dec. 18, 2020

(86) PCT No.: PCT/US2020/065973
§ 371 (c)(1),
(2) Date: Jun. 15, 2022

(87) PCT Pub. No.: WO2021/127407
PCT Pub. Date: Jun. 24, 2021

(65) Prior Publication Data

US 2023/0024928 A1 Jan. 26, 2023

Related U.S. Application Data

(60) Provisional application No. 62/949,823, filed on Dec. 18, 2019.

(51) Int. Cl.

| | |
|---|---|
| ***A61K 31/4192*** | (2006.01) |
| ***A61K 9/00*** | (2006.01) |
| ***A61K 9/14*** | (2006.01) |
| ***A61K 47/59*** | (2017.01) |

(52) U.S. Cl.
CPC ........ *A61K 31/4192* (2013.01); *A61K 9/0048* (2013.01); *A61K 9/14* (2013.01); *A61K 47/593* (2017.08)

(58) Field of Classification Search
CPC .................................................. A61K 31/4192
See application file for complete search history.

(56) References Cited

U.S. PATENT DOCUMENTS

| | | | |
|---|---|---|---|
| 8,846,077 | B2 | 9/2014 | Dewitt |
| 9,872,913 | B2 | 1/2018 | Troiano et al. |
| 2016/0338959 | A1 | 11/2016 | Troiano et al. |
| 2018/0000885 | A1 | 1/2018 | Dewitt et al. |

OTHER PUBLICATIONS

Wikipedia, "Carboxyamidotriazole, Retrieved from <https://en.wikipedia.org/w/index.php?title+Carboxyamidotriazole&oldid=702112356>" Jan. 28, 2016.

*Primary Examiner* — John S Kenyon
(74) *Attorney, Agent, or Firm* — Sung IP Law PLLC

(57) ABSTRACT

The present disclosure relates to nanoemulsions of 5-amino-[4-(4-chlorobenzoyl)-3,5-dichlorobenzyl]-1,2,3-triazole-4-carboxamide (carboxy-amido-triazole or CAI), methods of preparing thereof, and their use in the treatment of inflammatory optic neuropathies.

16 Claims, 2 Drawing Sheets

Results

| | | | Diam. (nm) | % Intensity | Width (nm) |
|---|---|---|---|---|---|
| Z-Average (d.nm): | 1460 | Peak 1: | 161 | 74.7 | 16.4 |
| PdI: | 1.000 | Peak 2: | 27.2 | 25.3 | 3.31 |
| Intercept: | 1.04 | Peak 3: | 0.00 | 0.0 | 0.00 |

Results

| | | | Diam. (nm) | % Intensity | Width (nm) |
|---|---|---|---|---|---|
| Z-Average (d.nm): | 215 | Peak 1: | 230 | 96.5 | 84.8 |
| PdI: | 0.223 | Peak 2: | 4820 | 3.5 | 715 |
| Intercept: | 0.971 | Peak 3: | 0.00 | 0.0 | 0.00 |

CAI NANOEMULSIONS

CROSS-REFERENCE TO RELATED APPLICATION

This application is a 35 USC § 371 National Stage application of International Application No. PCT/US2020/065973 filed Dec. 18, 2020, now pending; which claims the benefit under 35 USC § 119(e) to U.S. Application Ser. No. 62/949,823 filed Dec. 18, 2019. The disclosure of each of the prior applications is considered part of and is incorporated by reference in the disclosure of this application.

FIELD OF THE INVENTION

The present disclosure relates to nanoemulsions of 5-amino-[4-(4-chlorobenzoyl)-3,5-dichlorobenzyl]-1,2,3-triazole-4-carboxamide (carboxy-amido-triazole or CAI), methods of preparing thereof, and their use in the treatment of inflammatory optic neuropathies.

BACKGROUND 5-amino-1,2,3-triazole-4-carboxamide derivatives were originally discovered as antiparasitic agents and then subsequently demonstrated to be antiproliferative agents and potential cancer therapeutics. The specific compound, 5-amino-[4-(4-chlorobenzoyl)-3,5-dichlorobenzyl]-1,2,3-triazole-4-carboxamide (Formula I below), has been demonstrated to have antiproliferative and antimetastatic activity that was linked to decrease of intracellular calcium by inhibition of non-voltage-gated calcium channels. Tyrosine kinase and metalloproteinase pharmacological mechanistic activities and antiangiogenesis activity relevant to antitumor efficacy have also been described for this compound. The compound of Formula I will be referred to in the following discussion using the acronym CAI (carboxy-amido-triazole) which is generally used to describe the compound.

(I)

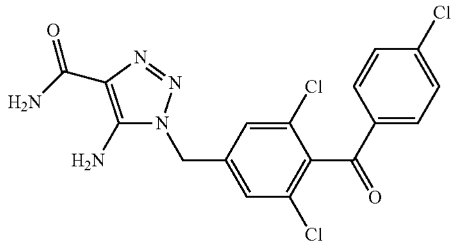

Clinical investigations have been conducted with CAI in the treatment of life-threatening diseases. For example, CAI has been used in the treatment of a variety of refractory tumors, including prostate cancer, lymphomas, glioblastoma, peritoneal cancer, fallopian tube cancer, epithelial ovarian cancer, advanced renal cell carcinoma, metastatic renal carcinoma, and non-small cell lung cancer (Bauer, K. S. et al Clin Cancer Res. 5:2324-2329, 1999; Kohn, E. C. et al Cancer Res. 52:3208-3212, 1992; Kohn, E. C. et al. J Biol Chem. 269:21505-21511, 1994a; Kohn, E. C. et al. Proc Natl Acad Sci USA. 92:1307-1311, 1995; Kohn, E. C. et al. Cancer Res. 56:569-573, 1996; Kohn, E. C. et al. J Clin Oncol. 15:1985-1993, 1997; Kohn, E. C. et al. Clin Cancer Res. 7:1600-1609, 2001.

While these studies using CAI indicate that CAI has intrinsic clinical efficacy for many cancer types, the systemic oral dosage regimens and formulations used in a clinical setting to date have been associated with dose limiting side effects. Moreover, toxic effects (cerebellar ataxia, peripheral neuropathy and exacerbation of depression) have been observed in clinical studies at doses of CAI required to achieve circulating levels that are within a narrow range or those projected from pharmacological studies to be required for effective inhibition of pathological neovascularization.

Furthermore, a serious side effect associated with clinical use of CAI by systemic administration has been the loss of vision for which two cases have been described (Berlin, J. et al. Clin Cancer Res. 8:86-94, 2002). Therefore, use of CAI as currently applied in clinical investigations for cancer is effectively precluded for acute or chronic treatment of non-life-threatening conditions, in particular for the treatment of ocular diseases described herein.

To treat certain ocular diseases, such as age-related macular degeneration (or AMD), and diabetic retinopathy, or diseases with specific ocular manifestations, such as von Hippel landau syndrome, therapeutic treatments rely on occlusion of the blood vessels using either threshold laser photocoagulation, or subthreshold laser combined with a photoactivated dye. However, such treatment requires either full-thickness retinal damage by thermal destruction, or damage to medium and large choroidal vessels thereby precluding any potential visual recovery. Further, the subject is left with a scar and visual scotoma. Moreover, recurrences are common, and visual prognosis is poor.

Recent research in the treatment of neovascularization has had the aim of causing more selective closure of the blood vessels, in order to preserve the overlying neurosensory retina. Such strategies have been used for the treatment of diabetic retinopathy, the leading cause of blindness among working age adults in Europe and the United States. However, extensive ocular tissue damage can occur after panretinal photocoagulation, with the visual handicap of more limited peripheral vision and poor night vision. With focal laser treatment, photocoagulation often can further compromise macular blood flow. Alternatively, a variety of molecules are in development or have been approved that target angiogenic pathways (e.g. the VEGF pathway). Thus, using antiangiogenic compounds is an alternative to lasering of patients.

CAI is an antiangiogenic compound; however, the poor aqueous solubilities of CAI means that novel methods of administration and targeted administration of it are required for providing safe and effective doses to treat disease and non-life-threatening diseases in particular.

High local concentrations of CAI may be required to treat acute disease symptoms while lower concentrations can be effective as continuation therapy or prophylactic therapy. Additionally, the frequency of administration of a CAI formulation of the present disclosure can also be used to ensure safe and effective local concentrations to slow vascular outgrowth. Treatment may be necessary from every week, to every month to few months, to yearly dosing with appropriate molecules in sustained delivery systems.

Treatments using dosage regimens, routes of administration and formulations of CAI described to date do not have adequate safety for treating severe proliferative diseases that are non-life-threatening. There exists an unfulfilled need for new dosage regimens, routes of administration and formulations of CAI that can provide therapeutic effects on non-life-threatening proliferative diseases, as exemplified by ocular diseases that are characterized by neovascularization and pathological cellular proliferation and invasion.

SUMMARY

The present disclosure provides a nanoemulsion formulation comprising 5-amino-[4-(4-chlorobenzoyl)-3,5-dichlorobenzyl]-1,2,3-triazole-4-carboxamide (CAI) and poly(D, L-lactic-co-glycolic acid) (PLGA), wherein the average particle size is less than 300 nm.

According to some embodiments of the present disclosure, the average particle size is less than 220 nm.

According to some embodiments of the present disclosure, the average particle size is less than 150 nm.

According to some embodiments of the present disclosure, the average particle size is 50 to 250 nm.

According to some embodiments of the present disclosure, the nanoemulsion formulation can further include 1% Tween 20.

According to some embodiments of the present disclosure, the nanoemulsion formulation can further include an ocular therapeutic substance selected from the group consisting of: a VEGF binding molecule and a tyrosine receptor kinase inhibitor.

According to some embodiments of the present disclosure, the VEGF binding molecule is selected from the group consisting of ranibizumab (Lucentis) and pegatanib (Macugen).

According to some embodiments of the present disclosure, the PLGA is from 7 kDa to 17 kDa and/or 66 kDa to 106 kD.

According to some embodiments of the present disclosure, the PLGA is from 7 kDa to 17 kDa.

According to some embodiments of the present disclosure, the PLGA is from 66 kDa to 106 kD.

The present disclosure further provides a method of treating a patient suffering from inflammatory optic neuropathies comprising: local ocularly administering to said patient a therapeutically effective amount of the nanoemulsion formulation.

According to some embodiments of the present disclosure, the method can further include diagnosing inflammatory optic neuropathies in said patient.

According to some embodiments of the present disclosure, the local ocular administration is by topical administration or ocular injection.

According to some embodiments of the present disclosure, the ocular injection is any one or combination of routes selected from the group consisting of periocular injection, sub-Tenon's injection, juxtascleral injection, intravitreal injection, subconjunctival injection, subretinal injection, and retrobulbar injection.

According to some embodiments of the present disclosure, the local ocular administration is assisted by sonophoresis or iontophoresis.

According to some embodiments of the present disclosure, the therapeutically effective amount of CAI is from 0.1 mg/mL to 100 mg/mL.

The present disclosure further provides a method of preparing the nanoemulsion formulation according to any of claims 1 to 10, comprising: (i) dissolving PLGA and CAI in acetonitrile; (ii) adding the acetonitrile solution from step (i) gradually over a first pre-determined time to an aqueous buffered salt solution (BSS) containing 1% Tween 20 while said BSS is agitated via high-speed vortexing; (iii) after step (ii) is complete, further agitating the resulting mixture via high-speed vortexing for a second pre-determined time; and (iv) removing the acetonitrile via evaporation to produce a nanoemulsion.

According to some embodiments of the present disclosure, the first pre-determined time is about 30 seconds to 2 minutes.

According to some embodiments of the present disclosure, the second pre-determined time is about 1 minute to 5 minutes.

DETAILED DESCRIPTION

Figure 1:
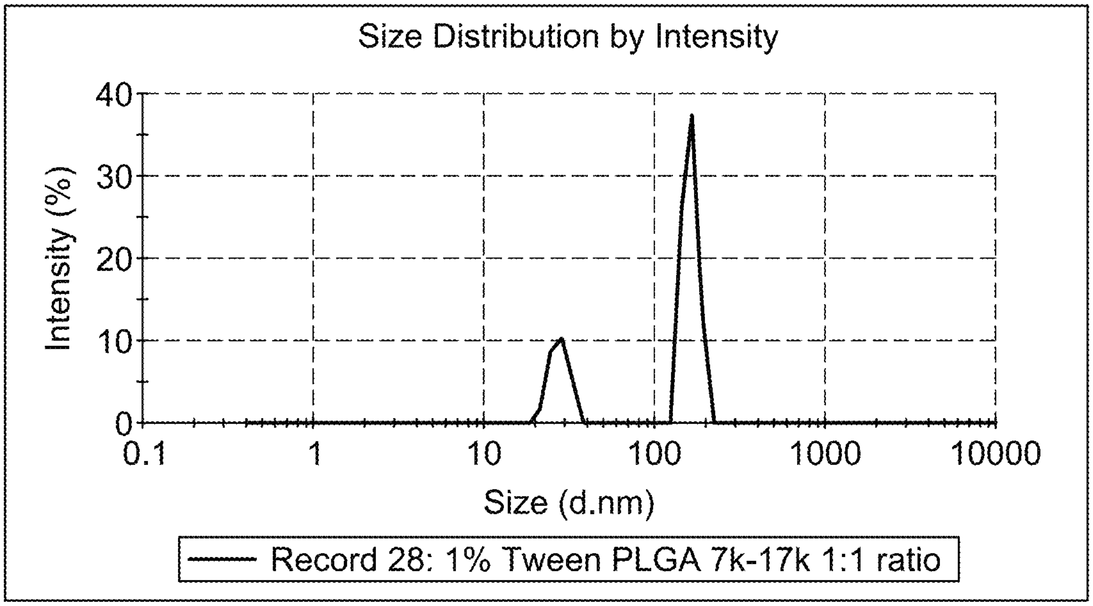
FIG. 1 shows a dynamic light scattering nanoparticle size profile of a CAI/PLGA formulation using low molecular weight PLGA (7 kDa to 17 kDa).

The present disclosure provides CAI formulations, methods of preparing thereof, and methods for their use in the localized treatment of non-life-threatening diseases. In particular, the present disclosure provides CAI nanoemulsion formulations, and further provides methods for treating non-life-threatening diseases comprising administering to a patient a therapeutically effective amount of a CAI formulation (using novel delivery systems and combination therapies) that are effective and are associated with little or no adverse side effects.

Routes of administration contemplated herein for the delivery of CAI formulations by local administration include, but are not limited to, ocular, dermal, nasal, ictic, pulmonary, intravitreal, peribulbar sub-Tenon, periocular, retrobulbar, subretinal, and posterior juxtascleral subconjunctival routes. Such routes of administration may be performed by injection by syringe and using a needle or cannula or by needle-free systems, including, but not limited to, topical administration via a formulation comprising drops, ointment, and creams, inhalation by means of an inhalation device such as a metered dose inhaler or dry powder inhaler or nebulizer, or in conjunction with drug delivery systems exemplified by controlled release of a CAI from a matrix comprising a contact lenses, (for delivery of drug to a tissue of the eye), from a device, from an implant, for release of drug to proximal tissue, and by use of an iontophoretic system e.g., to enhance the rate of penetration of drug through a barrier tissue.

Preferably, a CAI formulation is administered locally to ocular tissue via a route that attenuates ocular pathological disease processes without unduly compromising normal or healthy ocular function by acting directly in the eye (e.g., at the site of diseased tissue) in a controlled therapeutically effective and localized fashion.

The term "CAI" or "CAI compound," as used herein, refers to CAI as a free base and to CAI analogs, and CAI prodrugs, and to any salts such as acid salts thereof.

The term "therapeutically effective amount," as used herein, refers to the amount necessary to elicit the desired biological response such as amelioration or reduction in severity of a symptom by a percentage amount. In accordance with the present disclosure, the therapeutically effective amount of CAI is the amount necessary to treat non-life-threatening diseases. For some embodiments, an effective amount of a CAI formulation of the present disclosure may ameliorate the severity of symptoms and/or complications associated with a non-life-threatening disease. The amelioration in symptom and/or complication severity may be a 5%, 10%, 15%, 20%, 25% 30%, 35%, 40%, 45%, 50%, 55%, 60%, 65%, 70%, 75%, 80%, 85%, 90%, 95%, 98% or 99% decrease in severity. Preferably, the therapeutically effective amount of CAI locally administered in the treatment of ocular disease is a dose of 5 mg to 50 mg. More preferably 5 mg is dosed intravitreally and/or 50 mg is dosed periocularly. More preferably, the CAI compound is CAI free base in a nanoemulsion formulation.

The term "patient," as used herein, describes an organism, including mammals, to which treatment with the compositions according to the present disclosure is provided. Mammalian species that benefit from the disclosed compounds and methods of treatment include, but are not limited to apes, chimpanzees, orangutans, humans, monkeys; and domesticated animals (i.e., pets) such as horses, dogs, cats, mice, rats, guinea pigs, and hamsters.

The term "treatment" as used herein covers any treatment of a non-life-threatening disease in a patient, particularly a human, comprising administration of a CAI formulation of the present disclosure, and includes: (i) preventing the disease from occurring in a patient that may be predisposed to the disease but has not yet been diagnosed as having it; (ii) inhibiting the disease, e.g., inhibiting occurrence of an additional disease; or arresting development, inducing remission, or maintaining remission of the disease; (iii) relieving the disease, e.g., causing regression of the disease or addressing by diminishing or reducing symptoms; or (iv) inhibiting recurrence of a disease.

"Concurrent administration" and "concurrently administering," as used herein, includes administering a formulation of the present disclosure in a therapeutic method suitable for use with the methods of the present disclosure in the treatment of serious, non-life-threatening diseases. "Non-life-threatening disease(s)," as used herein, includes but is not limited to, non-life-threatening proliferative, inflammatory, neovascular, ocular, edematous, signal transduction-mediated diseases, matrix metalloproteinase-mediated diseases, and neurodegenerative diseases. Examples of serious, non-life-threatening ocular diseases include, but are not limited to diabetic retinopathy (DR), neovascular age-related macular degeneration (ARMD), diabetic macular edema (DME), cystoid macular edema (CME) and ocular tumors such as retinoblastoma (RB), Retinopathy of Prematurity (ROP), Retinal Vascular Occlusions (RVO), corneal neovascularization, iris neovascularization, neovascular glaucoma, ischemic neural damage, uveitis, glaucoma, and pterygium, neovascular diseases of the retina such as hyperproliferative retinopathies, vitreoretinopathies and retinal degeneration associated with systemic diseases such as diabetes mellitus, ischemic and hypoxic conditions associated with retinal vein and artery occlusion (e.g., from sickle cell disease or thrombosis), retinal degeneration resulting from retinal detachment, and age-related macular degeneration. Non-life-threatening diseases, as defined herein, include any disease that is directly or indirectly mediated by CAI. Non-life-threatening diseases are not diseases which may cause death in a patient. A non-life-threatening disease may be present in a patient together with a life-threatening disease such as diabetes mellitus.

The formulations of the present disclosure may also be used to treat ocular symptoms resulting from diseases or conditions that have both ocular and non-ocular symptoms. Some examples include AIDS-related disorders such as cytomegalovirus retinitis and disorders of the vitreous; von Hippel-Lindau Syndrome (a disease that has ocular and nonocular neovascularizations); pregnancy-related disorders such as hypertensive changes in the retina; and ocular effects of various infectious diseases such as tuberculosis, syphilis, Lyme disease, parasitic disease, *Toxocara canis*, ophthalmonyiasis, cysticercosis, and fungal infections. Examples of non-ocular diseases include, but are not limited to, rheumatoid arthritis, psoriasis, contact dermatitis, keratitis, conjunctivitis, scleritis, squamous cell carcinoma, condyloma, eczema, rosacea vascular proliferation associated with angioplasty, graft vs host disease (organ and tissue transplantation), glioblastoma, peripheral neuropathies, diabetic neuropathy, and collagen vasculidities.

In addition, the present disclosure can be used to treat diseases other than non-life-threatening diseases such as, but not limited to, bladder cancer, breast cancer, brain tumors, colon and rectal cancer, endometrial cancer, kidney cancer, leukemia, lung cancer, melanoma, non-Hodgkin's lymphoma, pancreatic cancer, prostate cancer, skin (non-melanoma) cancer, and thyroid cancer.

The present disclosure features formulations of CAI compounds for treatment of the non-life-threatening diseases. Such formulations serve to overcome bioavailability limitations of CAI as a poorly water-soluble compound and/or provide for the increased, with respect to an aqueous solution of free base CAI, bioavailability of free CAI drug to the targeted disease tissue and providing exposure to diseased tissue at a desired rate to achieve and maintain a therapeutically effective amount of CAI in a pharmacologically active concentration.

The nanoemulsion formulation comprises 5-amino-[4-(4-chlorobenzoyl)-3,5-dichlorobenzyl]-1,2,3-triazole-4-carboxamide (CAI) and poly(D,L-lactic-co-glycolic acid) (PLGA), wherein the average particle size is less than 300 nm. For some embodiments, the average particle size is less than 220 nm. For some embodiments, the average particle size is less than 150 nm. In some embodiments, the average particle size is from about 50 to 250, 50 to 150, 100 to 150, 100 to 300, 100 to 250, 125 to 250, 140 to 220, or 200 to 250.

The PLGA is from 7 kDa to 17 kDa and/or the PLGA is from 66 kDa to 106 kD. For some embodiments, the PLGA is from only 7 kDa to 17 kDa. For some embodiments, the PLGA is from 66 kDa to 106 kD.

For some embodiments, the nanoemulsion formulation further comprises 1% Tween 20. The nanoemulsion formulation can further include an ocular therapeutic substance selected from the group consisting of a VEGF binding molecule and a tyrosine receptor kinase inhibitor. For some embodiments, the VEGF binding molecule is selected from the group consisting of ranibizumab (Lucentis) and pegatanib (Macugen).

The nanoemulsion formulation can be prepared by a method, comprising: (i) dissolving PLGA and CAI in acetonitrile; (ii) adding the acetonitrile solution from step (i) gradually over a first pre-determined time to an aqueous buffered salt solution (BSS) containing 1% Tween 20 while said BSS is agitated via high-speed vortexing; (iii) after step (ii) is complete, further agitating the resulting mixture via high-speed vortexing for a second pre-determined time; and (iv) removing the acetonitrile via evaporation to produce a nanoemulsion.

The first pre-determined time is about 30 seconds to 2 minutes. For some embodiments, the first pre-determined time is about 1 minute.

The second pre-determined time is about 1 minute to 5 minutes. For some embodiments, the second pre-determined time is about 3 minutes.

For some embodiments, aqueous CAI formulations administered as described herein provide for immediate and complete release of CAI from a formulation. For some embodiments, aqueous CAI formulations of the present disclosure, when administered, provide for a slow rate of CAI release such as a controlled release or a zero order release or release of about 1% to 5% of the amount of administered drug over a time period of from about 1 hour to about 1 month. For some embodiments, the CAI formulations can include microemulsion and nanoemulsion formulations and polymer encapsulation formulations, wherein the drug can be dissolved or suspended in a matrix comprising a biocompatible and/or biodegradable polymer.

For some embodiments, the CAI formulations can include lyophilized microemulsion and nanoemulsion formulations in which an emulsion of the present disclosure has had water removed under reduced pressure at a low temperature, optionally in the presence of a cryoprotectant. See Rochelle do Vale Morais, et al., Freeze-drying of emulsified systems: A review, International Journal of Pharmaceutics (2016), Vol. 503, pgs. 102-114, the contents of which are incorporated by reference herein.

For some embodiments, the CAI formulations provide a slow rate of CAI release in the target disease tissue over a 1-week to 3-year period after a single administration. For some embodiments, the CAI formulations provide pharmacologically effective concentrations of CAI in the target disease tissue over a 15 minute to one-week period week after single administration.

The CAI formulations described below can be prepared in proportions of ingredients (CAI and pharmaceutically acceptable ingredients such as excipients, surface active agents, solvents, and the like) of which are determined by the solubility and chemical nature of the CAI compound or formulation, chosen route of administration, and standard medical practice. For example, microparticle formulations of CAI can be further prepared in an aqueous formulation, for example in the presence of a pharmaceutically acceptable surfactant or a pharmaceutically acceptable surface active agent.

Emulsion formulations of CAI compounds include, but are not limited to, compositions prepared using formulation processes comprising a lipid, surfactant and solvent that are readily performed by one skilled in the art of drug formulation. For some embodiments, emulsion formulations of CAI to be administered as described herein, provide for immediate or short term release of at least 90% of the amount of CAI in the formulation and providing pharmacologically effective concentrations of CAI in the target disease tissue over a 15 minute to one-week period week after single administration.

For some embodiments, the CAI nanoparticle formulation is prepared using methods that are standard in the art, such as by entrapment or encapsulation of CAI free base, CAI salt form or CAI prodrug drug molecules within a matrix or polymeric microspheres of sizes less than 300 nanometers, wherein the polymeric matrix material is selected from the group of albumin, polylactic-coglycolic acid, polymethacrylic acids and salts, polyethyleneglycol, natural polymeric materials, synthetic polymeric materials, charged polymeric materials, and uncharged polymeric materials, and combinations thereof. CAI free base, salt forms and prodrug molecules are described in U.S. Pat. Appl. Pub. No. 2011/0274748, the content of which is hereby incorporated by reference in its entirety.

For some embodiments, the polymer encapsulation systems include polylactic-coglycolic acid (PLGA) microsphere formulations as exemplified by the examples provided herein. Such formulations may be administered as a once-a-month depot injectable therapeutic.

CAI formulations of the present disclosure may contain pharmaceutically acceptable auxiliary substances as required to approximate physiological conditions, such as pH adjusting of an aqueous medium, for example to about pH 7.4, buffering agents to maintain such pH, tonicity adjusting agents to adjust tonicity of a formulation to physiological ionic strength, and wetting agents and the like, for example, sodium acetate, sodium lactate, sodium chloride, potassium chloride, calcium chloride, sorbitan monolaurate, triethanolamine oleate, etc.

The pharmaceutical formulations of the present disclosure may include delivery-enhancing agents that can be used alone, in combination with each other, or in combination with another delivery-enhancing agent. The term "delivery enhancing agents" includes agents that facilitate the transfer CAI to the target cell. Examples of such delivery enhancing agents include, but are not limited to, fatty acid esters, surfactants, detergents, alcohols, glycols, surfactants, bile salts, heparin antagonists, cyclooxygenase inhibitors, hypertonic salt solutions, acetates.

As contemplated herein, alcohols that can act as delivery enhancing agents include, without limitation, the aliphatic alcohols such as ethanol, N-propanol, isopropanol, butyl alcohol, and acetyl alcohol. Glycols that can act as delivery enhancing agents in accordance with the present disclosure include, but are not limited to, glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents.

Examples of pharmaceutically acceptable surfactants that can be provided in pharmaceutical formulations of the present disclosure include, without limitation, sodium dodecyl sulfate (SDS) and lysolecithin, polysorbate 80, nonylphenoxypolyoxyethylene, lysophosphatidylcholine, polyethyleneglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycocheno-deoxycholic acid and other astringents like silver nitrate may be used. Heparin-antagonists like quaternary amines such as prolamine sulfate may also be used. Additionally, cyclooxygenase inhibitors such as sodium salicylate, salicylic acid, and non-steroidal anti-inflammatory drug (NSAIDS) like indomethacin, naproxen, diclofenac may be used.

Examples of pharmaceutically acceptable detergents that can be provided in pharmaceutical formulations of the present disclosure can be selected from anionic, cationic, zwitterionic, and nonionic detergents. Exemplary pharmaceutically acceptable detergents include but are not limited to taurocholate, deoxycholate, taurocleoxycholate, caylpyridium, benalkonium chloride, ZWITTERGENT-3-14 detergent, CHAPS (3-{(3-Cholamidopropyl) dimethylammoniol}-1-propanesulfonate hydrate, Aldrich), Big CHAP, Deoxy Big CHAP, TRITON X-100 detergent, C12E8, Octyl-B-D-Glucopyranoside, PLURONIC-F68 detergent, TWEEN®-20 detergent, and TWEEN®-80 detergent.

The concentration of a delivery-enhancing agent in a pharmaceutical formulation of the present disclosure will depend on a number of factors known to one of ordinary skill in the art. Such factors include the particular delivery-enhancing agent being used, they buffer, pH, target tissue or organ and mode of administration. For some embodiments, the concentration of the delivery-enhancing agent will be in the range of 1% to 50% (v/v), preferably 10% to 40% (v/v) and most preferably 15% to 30% (v/v). Preferably, the detergent concentration in the final formulation administered to the patient is about 0.5 time to about 2 times the critical micellization concentration (CMC).

Excipients can be included in the formulations of the present disclosure. Examples include cosolvents, surfactants, oils, humectants, emollients, preservatives, stabilizers and antioxidants. A pharmacologically acceptable buffer may be used, e.g., tris or phosphate buffers. Effective amounts of diluents, additives and excipients are those amounts which are effective to obtain a pharmaceutically acceptable formulation in terms of solubility, stability, and biological activity.

Formulations of the present disclosure may also include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various commercially available pharmaceutically-acceptable saline, organic or inorganic salt solutions, Ringer's solution, dextrose solution, and Hank's solution. In addition, the pharmaceutical composition or formulation may include additives such as other carriers, adjuvants, or nontoxic, nontherapeutic, nonimmunogenic stabilizers and the like.

Carrier employed may be, for example, either a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. Similarly, a carrier for oral use may include time delay material well known in the art, such as glyceryl monostearate or glyceryl distearate alone or with a wax.

The CAI formulations of the present disclosure can be formulated according to known methods for preparing pharmaceutically useful compositions. Formulations are described in a number of sources, which are well known and readily available to those skilled in the art. For example, Remington's Pharmaceutical Science (Martin E W [1995] Easton Pa., Mack Publishing Company, $19^{th}$ ed.) describes formulations that can be used in connection with the present disclosure. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the present disclosure can include other agents conventional in the art having regard to the type of formulation in question.

Some embodiments of the present disclosure may be formulated for local instillation in or around tissue or organs, where for specific targeted local therapy for non-ocular body sites, parenteral therapy is used to achieve safe and effective local drug concentrations into a defined target lesion or disease area, or tissue(s), or organ(s), or body compartment(s), wherein routes of administration of formulations of CAI can include transcutaneous, subcutaneous, intradermal, intrathecal, intracerebellar, intramuscular, intra-articular or intravenous, when such direct application is practical and clinically indicated.

Some embodiments of the present disclosure may be formulated for systemic administration to a patient diagnosed with a non-life-threatening disease. Some embodiments of the present disclosure can be designed to locally deliver bioactive CAI into target eye tissue from implants to be injected in or around the eye, for sustained delivery of bioactive CAI to the eye. Delivery vehicles can also be designed in the form of ointments or gels or viscous suspensions or viscous emulsions that releases the drug upon administration into or around eye for prolonged periods to elicit the desired pharmacological action. The dosage form can also be a free flowing sterile suspension for topical administration or free flowing sterile suspensions for injection into or around eye.

The delivery system for a formulation of the present disclosure is in a pharmaceutically acceptable carrier, preferably a pharmaceutically acceptable aqueous carrier, suitable for local tissue compatibility. A variety of aqueous carriers may be used, e.g., water, buffered water, 0.8% saline, 0.3% glycine, hyaluronic acid and the like. Such delivery systems may be sterilized by conventional, well known sterilization techniques, e.g., by heat or steam sterilization of formulations in sealed vials at about 130° C. for at least 15 minutes, or liquid formulations may be sterile filtered, e.g., by filtration through a 0.2 micron filter in a sterile pharmaceutic environment.

The preferred routes of localized administration for the treatment of ocular diseases using the CAI formulations of the present disclosure include ophthalmic artery administration, subretinal injection, intravitreal injection, and periocular injection or juxtascleral administration. In the case of angiogenic diseases such as age related macular degeneration and diabetic retinopathy, the formulations of the present disclosure are administered over a course of treatment ranging from weeks to years. The preferred routes of administration for the treatment of such diseases include ophthalmic artery administration, subretinal injection, intravitreal injection, and periocular injection or juxtascleral administration. Sustained release formulations such as implants would also be appropriate for the treatment of such long term disease indications. These formulations may also be administered in combination with other anti-angiogenic agents.

For some embodiments, a CAI formulation can be injected intraocularly using intravitreal (into the vitreous), subconjunctival (into the subconjunctival), subretinal (under the retina), or retrobulbar (behind the eyeball) injection. For subconjunctival injection, a CAI dose in the range of about 0.1 ng/ml to about 10 mg/ml may be used. For intravitreal injection, a CAI dose in the range of about 0.1 ng/0.1 ml to about 10 mg/0.1 ml may be used. For retrobulbar injection, a CAI dose in the range of about 1 ng/ml to about 10 mg/ml may be used. For subretinal injection, a CAI dose in the range of about 0.1 ng/0.1 ml to about 10 mg/0.1 ml may be used.

Slow or extended-release delivery systems, such as delivery systems comprising a biopolymer (biological-based systems), liposomes, colloids, resins, and other pharmaceutical acceptable polymeric delivery systems or compartmentalized reservoirs, can be utilized with the formulations described herein to provide a continuously releasing or long term releasing source of therapeutic compound. Such slow release systems are applicable to formulations for delivery via topical, intraocular, oral, and parenteral routes. Delivery to areas within the eye, in situ can be accomplished by injection such as by using a needle and syringe, by use of a cannula or other invasive device designed to introduce precisely metered amounts of a desired formulation to a particular compartment or tissue within the eye (e.g. anterior or posterior chamber, uvea or retina). A solid, semisolid, or liquid implant can be delivered subretinally using the instrumentation and methods described in U.S. Pat. Nos. 5,817,075 and 5,868,728, the contents of which are hereby incorporated by reference in their entirety.

In a time-release formulation, the microsphere, capsule, liposome, etc. may contain a concentration of CAI that could be toxic if it were administered as a bolus dose. The time-release administration, however, is formulated so that the concentration released over any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, genetic makeup, etc.).

Depending upon the amount of CAI provided in the formulation and the release rate of the CAI, a patient could be dosed with CAI over a period of years from a single implant or injection that includes CAI. As illustrative but non-limiting examples, a capsule or a device, e.g., for implantation use, can be loaded with a CAI-based formulation comprising a concentration within the range of 1 to 200 mg of active CAI ingredient (e.g., 1 mg, 2 mg, 5 mg, 10 mg, 40 mg, 80 mg, 100 mg, 121 mg, 155 mg, 200 mg); if the capsule is formulated to release a small amount (e.g., 1 to 100 micrograms) of CAI active ingredient drug per day, the patient's disease could be treated for a period ranging from about 7-1,000 days (1-week to about 3-years) via a single administration of the capsule or device. Such a formulation provides benefits which include accurate dosing with heightened patient convenience, because frequent intervention or administration is not required, rather administration can be done in some cases only once or twice a decade or even less frequently. The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety.

Dosage Forms

Depending on the clinical needs of a patient, formulations of the present disclosure are prepared to either locally deliver bioactive CAI immediately after administration or for bioactive CAI release into a target tissue (for example, eye tissue) from its vehicle in a sustained manner over a period of time suitable for the desired pharmacological action.

An effective quantity of the compound of interest is employed in treatment. The dosage of compounds used in accordance with the present disclosure varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. In the case of angiogenic diseases such as age related macular degeneration and diabetic retinopathy, the formulations of the present disclosure are administered over a course of treatment ranging from weeks to years.

Combination Therapies

For some embodiments, the local administration of a CAI formulation can be concurrent with other pharmacological therapies for the treatment of non-life-threatening diseases. For example, a CAI formulation of the present disclosure can be administered concurrently with other clinical therapies such as the concurrent administration with anti-angiogenic compounds (e.g., combretastatin, angiostatin, endostatin, vitaxin, 2ME2, anecortave, squalamine, macugen, lucentis, PEDF), which may have diverse mechanisms of action (e.g. VEGF neutralization, tyrosine receptor kinase glucocorticoids and non-steroidal anti-inflammatory drugs.

The present disclosure provides for the concurrent, localized administration of therapies and a CAI formulation thereof, wherein the therapy addresses a non-life-threatening disease (such as certain non-cancerous proliferative and angiogenic diseases) other than that treated by the CAI formulation. For example, some embodiments provide the topical delivery of a CAI formulation for treating severe dermatological diseases including severe psoriasis, eczema and rosacea and local intraarticular administration for severe arthritis by inhibiting vascular and inflammatory cell proliferation.

Some embodiments provide for the treatment of neovascular and edematous ocular diseases by ocular administration of a CAI formulation, as described herein, in combination with other pharmacological anti-angiogenesis therapies. Contemplated anti-angiogenesis therapies comprise those which include, but are not limited to, glucocorticoids (preferred glucocorticoids include, dexamethasone, fluorometholone, administration of medrysone, budesonide, betamethasone, fluocinolone, triamcinolone, triamcinolone acetonide, prednisone, prednisolone, hydrocortisone, rimexolone, and pharmaceutically acceptable salts thereof), anecortave acetate, VEGF-binding molecules (oligonucleotide aptamers (e.g. Macugen™), protein antibodies (e.g. Lucentis™), tyrosine receptor kinase inhibitors, including but not limited to, vascular endothelial growth factor (VEGF), platelet derived growth factor (PDGF), and fibroblast growth factor (FGF) receptors, and other direct or indirect growth factor inhibitors including somatostatin receptor agonists (inhibiting release of Growth Hormone and IGF-1), RNAi oligonucleotide transcription inhibitors of ocular disease molecular targets including growth factors described above.

Active agents suitable for concurrent administration with a CAI formulation of the present disclosure include, but are not limited to: anti-infectives, including, without limitation, antibiotics, antivirals, and antifungals; antiallergenics and mast cell stabilizers; steroidal and non-steroidal anti-inflammatory agents; cyclooxygenase inhibitors, including, without limitation, Cox I and Cox II inhibitors; combinations of anti-infective and anti-inflammatory agents; anti-glaucoma agents, including, without limitation, adrenergics, beta-adrenergic blocking agents, alpha-adrenergic agonists, parasympathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil and angiostatic steroids for the treatment of diseases or conditions of the posterior segment of the eye, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592, which are incorporated herein in their entirety by reference. Preferred ones of such angiostatic steroids include 4,9(11)-Pregnadien-17α, 21-diol-3,20-dione and 4,9(11)-Pregnadien-17α, 21-diol-3,20-dione-21-acetate. A preferred non-steroidal anti-inflammatory for the treatment of cystoid macular edema is nepafenac.

Some embodiments provide for treatment or proliferative and edematous diseases via concurrent administration of CAI and an anti-angiogenic compound. Diverse anti-angiogenic compounds can be used in a combinatorial treatment of the present disclosure, include those with diverse mechanisms of action (e.g. VEGF neutralization, tyrosine receptor kinase inhibition, arachidonate inhibition, and Bcl-2 upregulation), such as glucocorticoids, non-steroidal anti-inflammatory drugs.

Some embodiments provide for the local administration of a CAI formulation of the present disclosure in combination with other pharmacological therapies specifically designed to provide efficacy with limited side effects, e.g. neuroprotectant agents, inhibitors of drug efflux, metabolite inhibition, synergistic agents, and agents designed to decrease specific side effects.

Some embodiments provide for the treatment of ocular diseases such as glaucoma and inflammatory eye disease by ocular administration of the CAI formulation, as described herein, in combination with other pharmacological agents including, but are not limited to, verteporfin photodynamic therapy (QLT Pharmaceuticals), anecortave acetate (Alcon Research Ltd.), Macugen (Eyetech Pharmaceuticals), Lucentis (ranibizumab, Genentech), Squalamine lactate (Genaera Corporation), LY333531 (Eli Lilly), and Fluocinolone (Bausch & Lomb), timolol, brimonidine, cyclosporine, cis-platin, carboplatin, methotrexate, steroids, BDNF, CIF, and INF-α blockers such as thalidomide and its derivatives and prodrugs.

Dexamethasone has been detected at 13 ng/ml in the vitreous cavity following a single 5 mg peribulbar injection in humans (Weijtens et al Ophthalmology 107(10) 1932-8 2000; Weijtens et. al Am J Ophthalmol 128(2): 192-7 1999). This results in a vitreous concentration of approximately 0.10-0.13 μM assuming a vitreous volume of 4-5 mL. Delivery to the subretinal space is 10-fold higher following subconjunctival injection (Weijtens et al Am J Ophthalmol 123(3): 358-63(1997)). The serum half-life of dexamethasone (18-36 hours) is significantly shorter than that of CAI (111 hours). Physiological tissue concentrations of CAI are in the 1-10 μM range so that it appears reasonable to postulate based on the scleral permeability and prolonged serum half-life of CAI that it can be effectively delivered transsclerally to the subretinal space. and the vitreous cavity in physiological concentrations (Weijtens et al Ophthalmology 107(10): 1932-8 2000; Weijtens et al Am J Ophthalmol 128(2): 192-7 1999). The release rates of the CAI formulations from sustained release devices are also favorable.

The present disclosure also contemplates the use of a glucocorticoid and/or neuroprotective agent in combination with the CAI formulation. A glucocorticoid alone and/or neuroprotective agent in combination with the CAI formulation is useful for treating persons suffering from pathologic ocular angiogenesis, in particular, exudative AMD and/or PDR, as well as subretinal or retinal edema associated with either condition. In addition to being effective in inhibiting the neovascularization associated with wet AMD and PDR, a CAI formulation of the present disclosure could be useful in controlling any IOP use associated with the use of a glucocorticoid, or to protect the retina from ischemic damage associated with microangiopathy or retinal vascular occlusions.

Delivery Devices

Some embodiments provide the use of a CAI formulation of the present disclosure in conjunction with a drug delivery system in the form of an implant or a device for treatment of conditions as set forth herein.

The present disclosure also provides the CAI formulation for use as a coating in conjunction with physical material implants such as stents and band ligatures used to treat vascular diseases. Preferably, stents coated with a CAI formulation of the present disclosure are used in the treatment of vascular disorders such as restenosis or vascular occlusion following vascular insult (e.g., angioplasty, alto- or xenotransplant vasculopathies, variceal bleeding, and transplantation of an organ).

An intraocular insert currently available for delivery of ganciclovir to the eye can also be used to deliver the CAI formulation of the present disclosure. Known as Vitrasert®, the device consists of a nonerodible, polymer-based, sustained-release package containing ganciclovir, a non-proteinaceous nucleoside analog. The device is surgically implanted in the vitreous humor of the eye to treat cytomegalovirus retinitis. See, e.g., Anand, R., et al., Arch. Ophthalmol., 111, pp. 223-227 (1993). Another intraocular insert is disclosed by U.S. Pat. No. 5,466,233. This tack-shaped device is surgically implanted so that the head of the tack is external to the eye, abutting the scleral surface. The post of the tack crosses the sclera and extends into the vitreous humor, where it provides for vitreal drug release.

A CAI formulation of the present disclosure may also be administered surgically as an ocular implant. As one example, a reservoir container having a diffusible wall of polyvinyl alcohol or polyvinyl acetate or partially hydrolyzed (e.g., about 1% to about 99% hydrolyzed) polyvinyl acetate and containing milligram (e.g., in the range of from about 1 mg to about 100 mg) quantities of nanoparticulate CAI may be implanted in or on the sclera. For example, U.S. Pat. No. 5,773,019, the contents of which is hereby incorporated by reference, discloses implantable controlled release devices for delivering drugs to the eye wherein the implantable device has an inner core containing an effective amount of a low solubility drug covered by a non-bioerodible polymer coating layer that is permeable to the low solubility drug. U.S. Pat. No. 5,378,475, the contents of which is hereby incorporated by reference, discloses sustained release drug delivery devices that have an inner core or reservoir comprising a drug, a first coating layer which is essentially impermeable to the passage of the drug, and a second coating layer which is permeable to the drug. The first coating layer covers at least a portion of the inner core but at least a small portion of the inner core is not coated with the first coating layer. The second coating layer essentially completely covers the first coating layer and the uncoated portion of the inner core. U.S. Pat. No. 4,853,224, the contents of which is hereby incorporated by reference, discloses biodegradable ocular implants comprising microencapsulated drugs for implantation into the anterior and/or posterior chambers of the eye.

The polymeric encapsulating agent or lipid encapsulating agent is the primary element of the capsule. U.S. Pat. No. 5,164,188, the contents of which is hereby incorporated by reference, discloses the use of biodegradable implants in the suprachoroid of an eye. The implants are generally encapsulated. The capsule, for the most part, is a polymeric encapsulating agent. Material capable of being placed in a given area of the suprachoroid without migration, "such as oxycel, gelatin, silicone, etc." can also be used U.S. Pat. No. 6,120,789, the contents of which is hereby incorporated by reference, discloses the use of a non-polymeric composition for in situ formation of a solid matrix in an animal, and use of the composition as a medical device or as a sustained release delivery system for a biologically-active agent, among other uses. Such implants can provide a CAI formulation of the present disclosure to a patient to treat a non-life-threatening disease.

Another implantable device that can be used to deliver formulations of the present disclosure is the biodegradable implants described in U.S. Pat. No. 5,869,079, the contents of which is hereby incorporated by reference. Additional intracorporeal devices to which a CAI formulation of the present disclosure can be added for example in the form of a coating include, but are not limited to, catheters, stents, angioplasty balloons, pacemakers, etc.

For some embodiments, methods are provided for expanding the lumen of a body passageway, comprising inserting a stent into the passageway, the stent having a generally tubular structure, the surface of the stent structure being coated with the CAI formulation, optionally in the presence of paclitaxel, such that the passageway is expanded. For some embodiments, methods are provided for eliminating biliary obstructions, comprising: inserting a biliary stent into a biliary passageway; for eliminating urethral obstructions, comprising inserting a urethral stent into a urethra; for eliminating esophageal obstructions, comprising inserting an esophageal stent into an esophagus; and for eliminating tracheal/bronchial obstructions, comprising, inserting a tracheal/bronchial stent into the trachea or bronchi. The stent has a generally tubular structure, and the surface of the structure can be coated with a composition comprising the CAI formulation and, optionally, together with other pharmaceutically active agents for a combination therapy.

Animal Efficacy and Safety Models

The CAI formulations, used directly or in conjunction with a drug delivery method or device as described herein, have highly advantageous therapeutic efficacy and safety for clinical use as local disease therapy when compared to systemic therapies of CAI described to date. The advantages a CAI formulation and administration methods of the present disclosure are provided by the controlled, efficacious and safe free CAI drug concentrations to the target tissue. The efficacy of the CAI formulation and drug delivery systems described herein to treat diseases described herein can be confirmed using standard in vivo animal test model of disease. These models include the mouse retinal neovascularization retinopathy of prematurity model (Smith L E et al. Invest Ophthalmol Vis Sci. 35(1):101-11, 1994), the method of which is hereby incorporated by reference, as well as the demonstration of an antiproliferative effect on choroidal endothelial cells and RPE in culture (Hoffman et at Ophthalmologe 2004), the method of which is hereby incorporated by reference. Further, the ability of the CAI formulation to provide controlled, safe levels suitable to treat human proliferative or neovascular ocular diseases can be confirmed using standard in vivo animal test ocular pharmacokinetic and pharmacodynamic studies in animals.

The CAI parent compound active ingredient, from which a CAI formulation described herein is derived, has demonstrated primary pharmacological action to decrease intracellular calcium concentration by inhibition of non-voltage-gated calcium channels (Kohn, E. C. et al. CAL Cancer Res. 54:935-942, 1994), thus affecting diverse signal transduction processes. Furthermore, the pharmacological mechanisms of action of CAI include, but are not limited to, the inhibition of disease mediating molecules including growth factors (e.g. VEGF), cytokines (e.g. IL-6), matrix metalloproteinases (MMps) and arachidonic acid (Felder, C. C et al. J Pharmacol Exp Ther. 257:967-971, 1991; Fox D A et al. Ann N Y Acad Sci.; 893:282-5, 1999; Cole K. et al. Cancer Metastasis Rev. March; 13 (1):31-44, 1994). These pharmacological mechanisms described for CAI provide the fundamental basis of antiproliferative activity on diverse cancer cell types (melanoma, breast, squamous, prostate, ovarian, glioblastoma, colon and small lung cell cancer) relevant to current clinical application of CAI as a systemically administered drug in life-threatening cancer indications. Furthermore, these pharmacological mechanisms described for CAI provide the fundamental basis of antiproliferative activity against other non-cancer cell types, including but not limited to human vascular and retinal endothelial cells, retinal pigment and choroidal endothelial cells ((Hoffman et al Ophthalmologe 2004), inflammatory cells including lymphocytes and eosinophils. Furthermore, since pathological increases in intracellular calcium (e.g. as mediated by pathological activation of NMDA receptor channels by excess glutamate in ischemic conditions) in neurons is known to result in neuronal death, it is anticipated by this of the present disclosure that administration of a CAI formulation as described herein can be neuroprotective.

The CAI formulations of the present disclosure, used directly or in conjunction with a drug delivery method or device as described herein, have highly advantageous therapeutic efficacy and safety for clinical use as local disease therapy when compared to systemic therapies of CAI described to date. The advantages of the CAI formulation and administration methods are provided by the controlled, efficacious, and safe free CAI drug concentrations administered to or reaching the target tissue. Plasma concentrations of CAI that have been associated with efficacy in cancer described in patients range from approximately 1.0 to 10 micromolar while plasma concentrations of above 100 micromolar can be associated with unacceptable toxicity. The present disclosure anticipates pharmacologically active concentrations of CAI as provided by the CAI formulation to exhibit therapeutic effects in the local target tissue to range between 0.5 and 100 micromolar. As a specific example, the present disclosure anticipates periocular administration of the CAI formulation, which contains 5 mg of active CAI ingredient, to provide CAI to the target subretinal and vitreal compartments in concentrations ranging from 0.1 and 10 micromolar concentration over a one-day time period. The ability of the CAI formulation to provide controlled, safe levels suitable to diseases described herein can be confirmed using standard in vivo pharmacokinetic studies in healthy animals or animal disease models. The formulation is administered as described herein and the samples of the target tissue are analyzed for concentration of CAI active principle using known or tissue adapted bioanalytical methods (e.g., Tutsch, K. D. et al. Proc Am Assoc Cancer Res. 37:A1133, 1996, the contents of which are hereby incorporated by reference in their entirety). For example, a CAI formulation containing 5 mg of active CAI ingredient is given to rabbits by periocular administration, and the animals are sacrificed at different time points over a 24 hour period. Tissue and liquid humor samples are taken from the eyes and the CAI active ingredient is extracted and subjected to HPLC-MS analysis with an appropriate internal standard to the target disease compartments including retinal, choroidal and vitreal compartments.

The efficacy of the CAI formulations, alone or in conjunction with drug delivery systems described herein to treat diseases described herein can be confirmed using in vivo animal test models of disease. These models include the mouse retinal neovascularization retinopathy of prematurity model (Smith L E et al. Invest Ophthalmol Vis Sci. 35 (1): 101-11, 1994, the methods of which are hereby incorporated by reference). In this model, mouse pups are placed into 75% $O_2$, along with their nursing dams, at post-natal day 7. They are maintained at this oxygen level for five days, at which point they are returned to normoxia. For the next five days, the pups are administered the CAI formulation of the present disclosure, using the methods described herein. At day 17, the animals are euthanized, enucleated, and the eyes fixed in 4% buffered paraformaldehyde overnight, then transferred to saline, embedded in paraffin, and sectioned. Serial sections are collected (6 micron sections, every $30^{th}$ section) and stained with hematoxylin and eosin. Individuals masked to the identity of treatment then count the number of pre-retinal nuclei and the effects CAI on lowering the number of pre-retinal nuclei are evaluated relative to control. At least eight sections are counted for each eye.

Another model is the adult mouse model of ischemia-induced choroidal neovascularization that mimics age-related macular degeneration. In this model, adult mice are subjected to laser photocoagulation in a manner similar to Ryan's (Ryan S J, et al., Trans Am Ophthalmol Soc. 77:707-745, 1979, the methods of which are hereby incorporated by reference). Three burn spots are produced in the choroid using an argon green wavelength laser at a power of 910-1030 mW for 0.05 sec to induce choroidal rupture and subsequent neovascularization. The burns are in three quadrants of the choroid, one disc area in diameter and one disc area from the optic nerve. This fixed distance allows the burns to be both reproducible and isolated from each other. The laser produces a bubble in the majority of cases, which is indicative of a Bruch's membrane rupture. In less than 5% of the animals, bleeding may be noted upon treatment. The mice are euthanized at two weeks after receiving laser photocoagulation and the eyes removed for evaluation of choroidal neovascularization.

Other disease models include xenograft models for host vs. graft tissue rejection relevant to applications including restenosis. Another object of the present disclosure is to provide for local treatment of other proliferative and angiogenic diseases including topical delivery of the CAI formulation for severe dermatological diseases—including severe psoriasis, eczema and rosacea and local intraarticular administration for severe arthritis by inhibiting vascular and inflammatory cell proliferation.

Therapeutic Applications

For some embodiments, a CAI formulation of the present disclosure can be used for administration to a human patient suffering from a non-life-threatening disease, as a method of treatment of such disease, which non-life-threatening disease can be, for example a proliferative disease, an inflammatory disease, an edematous disease, a neurodegenerative and/or a neurotoxic disease, or a signal transduction-mediated disease, or a matrix metalloproteinase-mediated disease.

Examples of diseases or disorders that can be mediated directly, or indirectly, by the administration of a CAI formulation of the present disclosure include, but are not limited to: age-related macular degeneration, diabetic retinopathy, retinal vascular occlusion, choroidal and retinal angiomatous proliferation, chronic glaucoma, retinal detachment, sickle cell retinopathy, rubeosis iritis, uveitis, neoplasms, Fuch's heterochromic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, retinal artery/vein occlusion, e.g., central retinal artery occlusion and branch retinal vein occlusion, contusive ocular injury, and retinopathy of prematurity, and other vascular anomalies, e.g., retinitis pigmentosa, endophthalmitis, infectious diseases, inflammatory but non-infectious diseases, ocular ischemia syndrome, peripheral retinal degenerations, retinal degenerations and tumors, choroidal disorders and tumors, vitreous disorders, retinal detachment, non-penetrating and penetrating trauma, post-cataract complications, and inflammatory optic neuropathies.

Hereditary degenerative retinal and vitreoretinal diseases treatable with a CAI formulation of the present disclosure, either alone or in combination therapies, include: Primary pigmented retinopathies, all gene types (ocular involvement only); Autosomal dominant retinitis pigmentosa e.g. rod-cone and cone-rod degenerations; Autosomal recessive retinitis pigmentosa e.g. rod-cone and cone-rode degenerations, Leber's amaurosis congenita; X-linked recessive pigmented retinopathies e.g. choroideremia. Secondary pigmented retinopathies (retinopathies associated with systemic diseases); Autosomal dominant pigmented retinopathies, e.g. Paget's disease, Charcot-Marie-Tooth disease, Steinert's disease, Pierre-Marie syndrome; Autosomal dominant pigmented retinopathies e.g. diabetes mellitus, mannosidoses, mucopolyscchari doses, Batten's disease, Refsum's disease, Usher syndrome; X-linked recessive pigmented retinopathies e.g. Hunter syndrome; conjunctivitis (e.g. allergic conjunctivitis, chronic conjunctivitis, contact lens-associated conjunctivitis, conjunctival ulceration, drug-related conjunctivitis); uveitis, uveoretinitis, chronic diseases (e.g. age-related macular panuveitis, retinitis, degeneration diabetes mellitus, infectious choroiditis, vitreitis, diseases (e.g., tuberculosis syphilis, cytomegalo-Scleritis/Episcleritis, virus retinitis), injury as a result of physical agents (e.g. UV Iridocyclitis, radiation), chemical agents (e.g. acids, Endophthalmitis caustic solvents), and immunological etiologies (e.g. sarcoidosis, inflammatory bowel disease, Corneal ulceration disease, and other collagen vascular diseases). Von Hippel-Lindau syndrome is a specific neovascular disease that has both ocular and non-ocular manifestations that should be treatable by a CAI formulation of the present disclosure.

The CAI formulations of the present disclosure may also be used to treat ocular symptoms resulting from diseases or conditions that have both ocular and non-ocular symptoms. Some examples include AIDS-related disorders such as cytomegalovirus retinitis and disorders of the vitreous; pregnancy-related disorders such as hypertensive changes in the retina; and ocular effects of various infectious diseases such as tuberculosis, syphilis, Lyme disease, parasitic disease, *Toxocara canis*, ophthalmonyiasis, cysticercosis, and fungal infections. Non ocular diseases can also include rheumatoid arthritis, psoriasis, contact dermatitis, keratitis, conjunctivitis, scleritis, squamous cell carcinoma and condyloma.

Angiogenesis and neovascularization in the adult animal is usually a pathological process, and is in direct contradistinction to non-pathological neovascularization, which usually occurs in normal embryogenesis (e.g., development of the embryonic vascular system). In accordance with the of the present disclosure, neovascularization refers specifically to pathological neovascularization. Aberrant or pathological vascularization is a key component in numerous disease states. For example, vascularization is a critical element of most solid tumors, such as cancers of the brain, genitourinary tract, lymphatic system, stomach, larynx and lung. These include histiocytic lymphoma, lung adenocarcinoma and small cell lung cancers. Aberrant vascular growth in the retina can lead to visual degeneration which can culminate in blindness. Accordingly, the of the present disclosure provides CAI formulations for the treatment of neovascularization.

Formulations of the present disclosure can also be used to inhibit the proliferation of vascular endothelial cells and so are indicated for use in treating graft vessel diseases such as restenosis or vascular occlusion following vascular insult such as angioplasty, alto- or xenotransplant vasculopathies, graft vessel atherosclerosis, and in the transplantation of an organ (e.g., heart, liver, lung, kidney or pancreatic transplants (Weckbecker et al., Transplantation Proceedings 1997, 29, 2599-2600).

The present disclosure also provides CAI formulations for the treatment of severe dermatological diseases including: severe psoriasis; contact dermatitis; eczema and rosacea; severe arthritis; and other vascular and inflammatory cell proliferative diseases (such as rheumatoid arthritis, spondyloarthropathies, gouty arthritis; osteoarthritis, systemic lupus erythematosus, juvenile arthritis, asthma, bronchitis, menstrual cramps, tendonitis, bursitis, skin related conditions such as psoriasis, eczema, burns, and dermatitis, gastrointestinal conditions such as inflammatory bowel disease, Crohn's disease, gastritis, irritable bowel syndrome and ulcerative colitis, colorectal cancer, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome; polymyositis; gingivitis; hypersensitivity; swelling occurring after injury; myocardial ischemia; and the like).

Additionally, disease states which rely on aberrant signal transduction/proliferation may also be treated by the CAI formulations. Diseases of potentially aberrant signal transduction/proliferation may include the collagen vasculitides (i.e., systemic lupus erythematosis and rheumatoid arthritis), neurologic diseases (i.e., dementia and nerve conduction diseases), diseases of transport (i.e., cystic fibrosis), toxic effects of agents (i.e., cisplatin-related neuropathy), and cellular dysfunction (i.e., myelodysfunction syndromes), hemangiomata, and collagen vasculidities.

For some embodiments, the CAI formulation can be provided by local ocular administration by means of periocular, retrobulbar, intravitreal, subretinal, posterior juxtascleral, topical and subconjunctival administration through injection or needle-free system, or topical administration though local instillation, drops, ointment, or in conjunction with drug delivery systems exemplified by contact lenses, devices and implants. Some embodiments provide the treatment of a broad range of ocular diseases including diabetic retinopathy (DR), neovascular proliferative age-related macular degeneration (ARMD), diabetic macular edema (DME), cystoid macular edema (CME) and ocular tumors such as retinoblastoma (RB), Retinopathy of Prematurity (ROP), retinal vascular occlusions (RVO), uveitis, glaucoma, corneal neovascularization, iris neovascularization, neovascular glaucoma, ischemic neural damage, and pterygium by the local ocular administration of the CAI formulation, directly or in conjunction with a drug delivery system as described herein.

Following are examples. which illustrate procedures for practicing the CAI formulations described above. These examples should not be construed as limiting.

EXAMPLES

Example 1. Preparation of CAI Nanoemulsions

In the following examples, CAI (5-amino-[4-(4-chlorobenzoyl)-3,5-dichlorobenzyl]-1,2,3-triazole-4-carboxamide) can be prepared by one skilled in the art of organic chemistry according to procedures described in U.S. Pat. Nos. 4,590,201 and 5,602,156; poly(lactic-co-glycolic acid) (PLGA) was purchased from Sigma-Aldrich (50:50 lactide: glycolide ratio, MW 7 kDa-17 kDa, Cat. No. 719897) or (75:25 lactide/glycolide ratio, MW 66 kDa-107 kDa, Cat. No. P1941); acetonitrile (99.8%, anhydrous) was purchased from Sigma-Aldrich (Cat. No. 271004); Tween® 20 was purchased from Sigma-Aldrich (Cat. No. P9416); and hydroxypropyl methylcellulose (HPMC) was purchased from Sigma-Aldrich (Cat. No. 09963); and water was type III quality water filtered through a Millipore filter with a pore size of 0.22 microns. Buffered salt solution (BSS buffer) was prepared by dissolving 6.40 g of NaCl, 0.75 g of KCl, 0.48 g of $CaCl_2 \cdot 2H_2O$ in 900 mL of water. For BSS solutions containing 1% Tween® 20, 10.0 g of this material was added. For BSS solutions containing 1% Tween® 20 and 1% HPMC, 10.0 g of each of these materials was added. The pH of the solution was checked with a pH meter and adjusted with either 0.1 M NaOH or 0.1 M HCl to a pH of 7.5, followed by dilution with additional water to a volume of 1000 mL.

Formulation 1—Low Molecular Weight PLGA Formulation

PLGA (7 kDa-17 kDa, 200 mg) was dissolved in 20 mL of acetonitrile. CAI (24 mg) was added and the solution was agitated by vortexing until complete dissolution was observed. This solution was added over 1 minute to 20 mL of BSS buffer containing 1% Tween® 20 being agitated in a vortexer at high speed and mixing was continued for 3 minutes after addition was complete. The particle size was assessed by dynamic light scattering using a Malvern Zetasizer Nano ZS instrument and found to have an average size of 146.0 nm. See FIG. 1.

Formulation 2—High Molecular Weight PLGA Formulation

Figure 2:
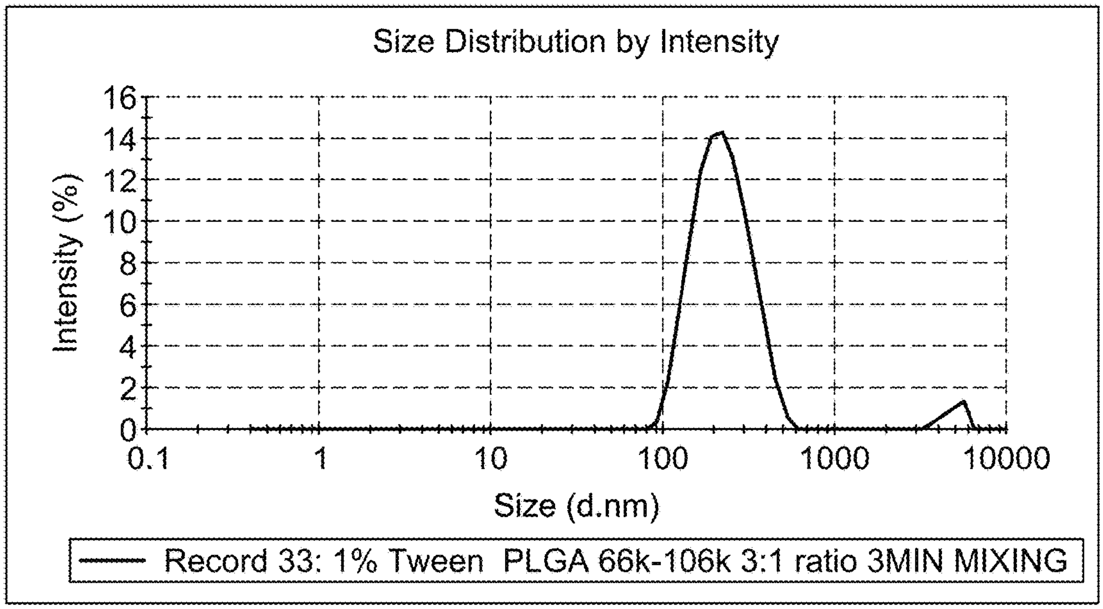
FIG. 2 shows a dynamic light scattering nanoparticle size profile of a CAI/PLGA formulation using high molecular weight PLGA (66 kDa to 106 kDa).

PLGA (66 kDa-106 kDa, 200 mg) was dissolved in 20 mL of acetonitrile. CAI (50 mg) was added and the solution was agitated by vortexing until complete dissolution was observed. This solution was added over 1 minute to 20 mL of BSS buffer containing 1% Tween® 20 being agitated in a vortexer at high speed and mixing was continued for 3 minutes after addition was complete. The particle size was assessed by dynamic light scattering using a Malvern Zetasizer Nano ZS instrument and found to have an average size of 215.0 nm. See FIG. 2.

For each of Formulations 1 and 2, the acetonitrile is removed from the resulting organic mixture described above by evaporation (e.g. under reduced pressure using a rotary evaporator). Once the acetonitrile is removed, BSS buffer is added to the resulting organic mixture to a desired concentration of CAI, and the pH is checked and adjusted to an acceptable therapeutically applicable range (preferably from about pH 3.0 to about pH 8.0; more preferably from about pH 5.0 to about pH 8.0; and most preferably a pH of 7-4 to 7.5) by addition of a basic solution (preferably aqueous sodium hydroxide) or an acidic solution (preferably aqueous hydrochloric acid) or both in quantities sufficient to provide the desired pH.

For each of Formulations 1 and 2, the resulting aqueous solution can be lyophilized after removal of acetonitrile. The resulting lyophilizate can then be reconstituted with an appropriate amount of water or water/BSS before use. The nanoparticulate CAI lyophilizate can be further formulated with other excipients as described elsewhere herein.

Stable sterile formulations can then be prepared by autoclaving for sufficient time at temperatures suitable for effectively killing the microorganisms that may be present in the formulation, for instance, 121° C. for about 30 minutes. After such a sterilization procedure, no decomposition of CAI or formation of new impurities could be detected by reversed-phase high pressure liquid chromatography (RP-HPLC) analysis using UV detection (Conditions: RP-18 column: 5 micron particle size, length=13 cm, diameter=8 mm; solvent system: solvent A=0.001% trifluoroacetic acid, solvent B=acetonitrile, gradient=8 0% A/20% B to 10% A/90% B over 12 min at a flow rate of 2.5 mL/min; CAI retention time=6.3 min).

Manufacturing stable sterile formulations can also be readily accomplished by filtration through sterile filtration membranes (e.g., 0.1 micron membranes, 0.2 micron membranes).

Example 2. Intravitreal Injection of CAI Nanoemulsions

In an intravitreal injection protocol, a pharmacologically effective concentration of CAI (0.5 to 10 micromolar concentration using a dose of 0.2 ng to 40 ng of CAI in a compartment of about 4 to 5 mL for the eye for a long term 4 to 6 week maintenance controlled dose use) is administered via the inferotemporal pars plana in a protocol similar to triamcinolone, Macugen®, or Lucentis®.

Example 3. Periocular Injection of CAI Nanoemulsions

In a periocular injection protocol, an initial dose of 5 to 50 mg of CAI is used for periocular administration. In a periocular injection protocol, a pharmacologically effective concentration of CAI (0.5 to 10 micromolar concentration using a dose of 0.2 ng to 40 ng of CAI in a compartment of about 10-20 mL for the eye for a long term 4 to 6 month maintenance controlled dose use) is administered into the subtenon's space in a protocol similar to triamcinolone.

Although the invention has been described with reference to the above examples, it will be understood that modifications and variations are encompassed within the spirit and scope of the invention. Accordingly, the invention is limited only by the following claims.

What is claimed:

1. A nanoemulsion formulation comprising 5-amino-[4-(4-chlorobenzoyl)-3,5-dichlorobenzyl]-1,2,3-triazole-4-carboxamide (CAI) and poly(D,L-lactic-co-glycolic acid) (PLGA), wherein the average particle size is less than 300 nm, and an ocular therapeutic substance selected from the group consisting of: a VEGF binding molecule and a tyrosine receptor kinase inhibitor.

2. The nanoemulsion formulation according to claim 1, wherein the average particle size is less than 220 nm.

3. The nanoemulsion formulation according to claim 1, wherein the average particle size is less than 150 nm.

4. The nanoemulsion formulation according to claim 1, wherein the average particle size is 50 to 250 nm.

5. The nanoemulsion formulation according to claim 1 further comprising 1% polyethylene glycol sorbitan monolaurate.

6. The nanoemulsion formulation according to claim 1, wherein said VEGF binding molecule is selected from the group consisting of ranibizumab (Lucentis) and pegatanib (Macugen).

7. The nanoemulsion formulation according to claim 1, wherein said PLGA is from 7 kDa to 17 kDa and/or 66 kDa to 106 kD.

8. The nanoemulsion formulation according to claim 1, wherein said PLGA is from 7 kDa to 17 kDa.

9. The nanoemulsion formulation according to claim 1, wherein said PLGA is from 66 kDa to 106 kD.

10. A method of treating a patient suffering from inflammatory optic neuropathies comprising: local ocularly administering to said patient a therapeutically effective amount of the nanoemulsion formulation according to claim 1.

11. The method according to claim 10, further comprising diagnosing inflammatory optic neuropathies in said patient.

12. The method according to claim 10, wherein said local ocular administration is by topical administration or ocular injection.

13. The method according to claim 12, wherein said ocular injection is any one or combination of routes selected from the group consisting of periocular injection, sub-Tenon's injection, juxtascleral injection, intravitreal injection, subconjunctival injection, subretinal injection, and retrobulbar injection.

14. The method according to claim 13, wherein said local ocular administration is assisted by sonophoresis or iontophoresis.

15. The method according to claim 10, wherein the therapeutically effective amount of CAI is from 0.1 mg/mL to 100 mg/mL.

16. A method of preparing the nanoemulsion formulation according to claim 1, comprising: (i) dissolving PLGA and CAI in acetonitrile; (ii) adding the acetonitrile solution from step (i) gradually over a first predetermined time to an aqueous buffered salt solution (BSS) containing 1% polyethylene glycol sorbitan monolaurate while said BSS is agitated via high-speed vortexing; (iii) after step (ii) is complete, further agitating the resulting mixture via high-speed vortexing for a second pre-determined time; and (iv) removing the acetonitrile via evaporation to produce a nanoemulsion.

* * * * *